(12) United States Patent
Chai et al.

(10) Patent No.: US 11,471,095 B2
(45) Date of Patent: Oct. 18, 2022

(54) TONGUE-IMAGE-BASED DIAGNOSTIC SYSTEM AND DIAGNOSTIC METHOD

(71) Applicant: BOE TECHNOLOGY GROUP CO., LTD., Beijing (CN)

(72) Inventors: Dong Chai, Beijing (CN); Suo Zhang, Beijing (CN); Hong Wang, Beijing (CN)

(73) Assignee: BEIJING BOE TECHNOLOGY DEVELOPMENT CO., LTD., Beijing (CN)

( * ) Notice: Subject to any disclaimer, the term of this patent is extended or adjusted under 35 U.S.C. 154(b) by 400 days.

(21) Appl. No.: 16/029,256

(22) Filed: Jul. 6, 2018

(65) Prior Publication Data
US 2019/0200918 A1 Jul. 4, 2019

(30) Foreign Application Priority Data

Jan. 3, 2018 (CN) .......................... 201810004287.3

(51) Int. Cl.
*A61B 5/00* (2006.01)
*G06T 7/00* (2017.01)
(Continued)

(52) U.S. Cl.
CPC .......... *A61B 5/4552* (2013.01); *A61B 5/0077* (2013.01); *A61B 5/0088* (2013.01);
(Continued)

(58) Field of Classification Search
CPC ......... A61B 5/4552; A61B 5/01; A61B 5/024; A61B 5/0816; A61B 5/4866;
(Continued)

(56) References Cited

U.S. PATENT DOCUMENTS

| 2004/0120557 A1* | 6/2004 | Sabol ..................... G09B 23/28 382/128 |
| 2017/0311872 A1 | 11/2017 | Matsuda |

FOREIGN PATENT DOCUMENTS

| CN | 203970354 U | 12/2014 |
| CN | 205625892 U | * 10/2016 |

(Continued)

OTHER PUBLICATIONS

Zhang, B., Wang, X., You, J., & Zhang, D. Tongue color analysis for medical application. 2013. Evidence-Based Complementary and Alternative Medicine, 2013. (Year: 2013).*

(Continued)

*Primary Examiner* — Jason M Ip
*Assistant Examiner* — Renee C Langhals
(74) *Attorney, Agent, or Firm* — Kinney & Lange, P.A.

(57) ABSTRACT

A tongue-image-based diagnostic system and a tongue-image-based diagnostic method are disclosed. The diagnostic system includes a parameter collector configured to acquire environmental parameter information; a model establishment circuitry configured to perform a training process using image training data and the environmental parameter information and establish an estimation model; and an analysis circuitry configured to analyze acquired image information using the estimation model, and generate an analysis result corresponding to the acquired image information.

18 Claims, 4 Drawing Sheets

(51) Int. Cl.
*A61B 5/01* (2006.01)
*A61B 5/024* (2006.01)
*A61B 5/08* (2006.01)
*G06T 3/20* (2006.01)
*G06T 3/60* (2006.01)
*G06T 7/11* (2017.01)
*H04N 5/235* (2006.01)
*G06K 9/62* (2022.01)

(52) U.S. Cl.
CPC .............. *A61B 5/01* (2013.01); *A61B 5/024* (2013.01); *A61B 5/0816* (2013.01); *A61B 5/4848* (2013.01); *A61B 5/4866* (2013.01); *A61B 5/7267* (2013.01); *G06K 9/6262* (2013.01); *G06K 9/6273* (2013.01); *G06T 3/20* (2013.01); *G06T 3/60* (2013.01); *G06T 7/0016* (2013.01); *G06T 7/11* (2017.01); *H04N 5/2351* (2013.01); *H04N 5/2354* (2013.01); *A61B 2560/0252* (2013.01); *G06T 2207/20081* (2013.01); *G06T 2207/30036* (2013.01); *G06V 2201/03* (2022.01)

(58) Field of Classification Search
CPC ... A61B 5/0077; A61B 5/0088; A61B 5/7267; A61B 5/4848; A61B 2560/0252; A61B 2560/0242; G06K 9/6273; G06K 9/6262; G06K 2209/05; G06T 3/20; G06T 3/60; G06T 7/11; G06T 7/0016; G06T 2207/20081; G06T 2207/30036; G06T 2207/20084; G06T 7/0012; H04N 5/2351; H04N 5/2354; H04N 5/2256; G16H 50/70
USPC .......................................................... 600/408
See application file for complete search history.

(56) References Cited

FOREIGN PATENT DOCUMENTS

| CN | 205625892 U | 10/2016 |
|---|---|---|
| CN | 106295139 A | 1/2017 |
| CN | 106725341 A | 5/2017 |
| CN | 106999045 A | 8/2017 |
| CN | 206403755 U | 8/2017 |
| CN | 107316307 A | 11/2017 |
| JP | 2006149679 A | 6/2006 |
| KR | 20170099066 A * | 8/2017 |

OTHER PUBLICATIONS

Liu, Z., Wang, H., & Li, Q. (2012). Tongue tumor detection in medical hyperspectral images. Sensors, 12(1), 162-174. (Year: 2012).*
First Chinese Office Action dated Jul. 3, 2020, for corresponding Chinese Application No. 201810004287.3.
Second Chinese Office Action dated Nov. 27, 2020, for corresponding Chinese Application No. 201810004287.3.

* cited by examiner

TONGUE-IMAGE-BASED DIAGNOSTIC SYSTEM AND DIAGNOSTIC METHOD

CROSS-REFERENCE TO RELATED APPLICATION

The present application claims a priority of the Chinese patent application No. 201810004287.3 filed in China on Jan. 3, 2018, the disclosure of which is incorporated herein by reference in its entirety.

TECHNICAL FIELD

The present disclosure relates to the field of an image processing technology, and in particular, relates to a tongue-image-based diagnostic system and a tongue-image-based diagnostic method.

BACKGROUND

With development of science and technology, more and more users perform prediction or precaution of diseases by themselves. During performing diagnosis on a tongue of a user, the user may predict his or her health condition through uploading an image of the tongue. However, during acquisition and analysis of the image of the tongue or any other image, the image may be adversely affected by environmental factors.

SUMMARY

The present disclosure provides a tongue-image-based diagnostic system and a tongue-image-based diagnostic method.

In a first aspect, a tongue-image-based diagnostic system is provided and includes a parameter collector configured to acquire environmental parameter information; a model establishment circuitry configured to perform a training process using received image training data and the environmental parameter information and to establish an estimation model, wherein the image training data includes first tongue image information for training; and an analysis circuitry configured to analyze acquired image information using the estimation model, and to generate at least an analysis result about a probability that a user related to the acquired image information suffers from a cancer, wherein the acquired image information includes a second tongue image information of a user to be diagnosed.

Optionally, the parameter collector includes: a temperature collector configured to collect temperature information, and a brightness collector configured to collect brightness information.

Optionally, the parameter collector further includes a physiological parameter collector configured to collect physiological parameter information, and the physiological parameter information includes at least one of body temperature information, respiratory rate information or heart rate information of a user, the model establishment circuitry is further configured to perform the training process using the received image training data, the environmental parameter information corresponding to the image training data and the physiological parameter information, and establish the estimation model.

Optionally, the parameter collector is further configured to acquire at least one of drug administration information or dietary parameter information of a user; and the model establishment circuitry is further configured to perform the training process using the received image training data, the environmental parameter information corresponding to the received image training data, and the at least one of the drug administration information or the dietary parameter information, and establish the estimation model.

Optionally, the diagnostic system further includes a data generation circuitry configured to perform an image conversion operation on the first tongue image information, and generate the image training data based one at least one of the first tongue image information or the converted first tongue image information.

Optionally the image conversion operation includes at least one of an image translation operation or an image rotation operation, or at least one of an image segmentation operation or an image annotation operation.

Optionally, the model establishment circuitry is further configured to validate the estimation model, and the analysis circuitry is further configured to, in a case that the model establishment circuitry successfully validates the estimation model, analyze the second tongue image information using the validated estimation model and generate the analysis result corresponding to the second tongue image information.

Optionally, the diagnostic system further includes an image collection assembly including an image collector and configured to acquire at least one of the first tongue image information or the second tongue image information through the image collector, and transmit the first tongue image information to the model establishment circuitry and transmit the second tongue image information to the analysis circuitry.

Optionally, the image collection assembly further includes: a light source configured to generate light; a light brightness sensor configured to collect a brightness value of the environment; and a brightness adjustment circuitry configured to: receive the brightness value from the light brightness sensor; compare the received brightness value with a predetermined brightness value; when the received brightness value is different from the predetermined brightness value, adjust the brightness value of the light generated by the light source until the brightness value collected by the light brightness sensor is a same as the predetermined brightness value; and when the brightness value collected by the light brightness sensor is the same as the predetermined brightness value, control the image collector to collect image information.

Optionally, the image training data further includes health condition data corresponding to the first tongue image information, and the health condition data includes information about a user suffers from the cancer or information about a probability that the user suffers from the cancer.

Optionally, the image collector is further configured to acquire an oral image of a user when acquiring the first tongue image information, and the model establishment circuitry is further configured to analyze the oral image.

Optionally, the model establishment circuitry is further configured to: validate the estimation model using a plurality of groups of validation data, wherein each group of validation data includes image information and a health estimation result corresponding to the image information; and when coherence of validation results of the plurality of groups of validation data with the health estimation result is greater than a predetermined probability, determine that the estimation model is validated successfully.

Optionally, the diagnostic system further includes a user management device configured to establish a link among the first tongue image information, the second tongue image information, and the analysis result from the analysis circuitry.

In a second aspect, a tongue-image-based diagnostic method is provided and includes: acquiring environmental parameter information; performing a training process using received image training data and the environmental parameter information, and establishing an estimation model, wherein the image training data includes a first tongue image information for training; and analyzing acquired image information using the estimation model, and generating an analysis result about a probability that a user corresponding to the acquired image information suffers from a cancer, wherein the acquired image information includes a second tongue image information of the user to be diagnosed.

Optionally, the environmental parameter information includes at least one of temperate information or brightness information; before performing a training process using received image training data and the environmental parameter information, and establishing an estimation model, the diagnostic method further includes acquiring at least one of physiological parameter information, drug administration information or dietary parameter information; and the performing a training process using received image training data and the environmental parameter information further includes performing the training process using the received image training data, at least one of (i) the temperature information or (ii) the brightness information, and at least one of (i) the physiological parameter information, (ii) the drug administration information or (iii) the dietary parameter information.

Optionally, before performing a training process using received image training data and the environmental parameter information, and establishing an estimation model, the diagnostic method further includes: acquiring the first tongue image information; performing an image conversion operation on the acquired first tongue image information; and generating the image training data using at least one of the first tongue image information and the converted first tongue image information.

Optionally, the performing an image conversion operation on the acquired first tongue image information, includes: performing at least one of an image segmentation operation and an image annotation operation on the first tongue image information, or performing at least one of an image translation operation and an image rotation operation on the first tongue image information.

Optionally, the diagnostic method further includes validating the estimation model; in a case that the estimation model is validated successfully, analyzing the second tongue image information using the validated estimation model; and generating the analysis result corresponding to the second tongue image information.

Optionally, the image training data further includes health condition data of a user corresponding to the first tongue image information, and the health condition data includes information about the user corresponding to the first tongue image information suffers from a cancer or information about a probability that the user suffers from the cancer.

In a third aspect, a tongue-image-based diagnostic system is provided and includes a processor, and a storage configured storing computer programs executable by the processor, wherein when the computer programs are executed by the processor, the processor performs steps in the diagnostic method according to the first aspect.

DETAILED DESCRIPTION

The present disclosure will be described in detail hereinafter in conjunction with drawings and the following embodiments. The following embodiments do not limit the scope of the present disclosure.

It should be appreciated that one skilled in the art may make various modifications to the embodiments of the present disclosure, and the contents provided herein do not limit the scope of the present disclosure, but are only examples of the embodiments of the present disclosure; one skilled in the art may make further modifications to the embodiments of the present disclosure without departing from the spirit and the scope of the present disclosure.

The drawings included in and constituting a part of the specification are illustrative of some embodiments of the present disclosure. These drawings and detailed description of the embodiments provided below together are used for explaining the principle of the present disclosure.

Optional examples of the embodiments of the present disclosure are described hereinafter in conjunction with the drawings. These and other features of the present disclosure will become apparent with reference to the description. The embodiments may be implemented in many ways. Known and/or repeated functions and structures are not described in details in the present disclosure, so as to avoiding obscurity of the present disclosure by unnecessary or superfluous details. Hence, structural and functional details described are not intended to limit the scope of the present disclosure, but are merely used to enable a person skilled in the art to implement the present disclosure through any substantially appropriate structure.

Such expressions as "in some embodiments" or "in the embodiments" involved herein are merely used to indicate one or more of same or different embodiments of the present disclosure.

The present disclosure provides a tongue-image-based diagnostic system in some embodiments. The tongue-image-based diagnostic system may analyze an inputted tongue image by using an established model (also called as an estimation model), and generate and output a health estimation result corresponding to the tongue image. The health estimation result includes information about a probability of a cancer (e.g., an esophagus cancer or an oral cancer). As a result, a user inputting the tongue image may diagnose a disease and detect a health condition by himself or herself. The estimation model may be established after a deep training process is performed. In some embodiments of the present disclosure, environmental parameters may be combined with the training process for establishing the estimation model, thereby to significantly increase an accuracy of the health estimation result.

Figure 1:
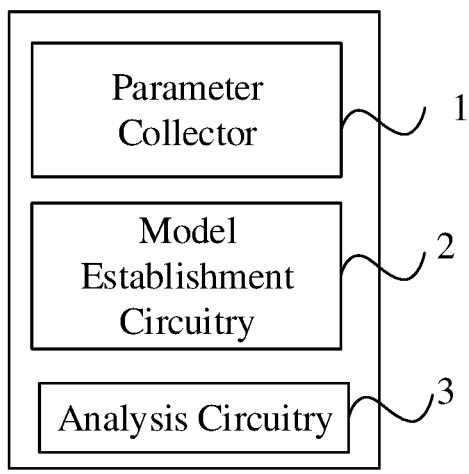
FIG. 1 is a structural schematic view of a tongue-image-based diagnostic system according to some embodiments of the present disclosure.

FIG. 1 is a structural schematic diagram of the tongue-image-based diagnostic system according to some embodiments of the present disclosure. As shown in FIG. 1, the tongue-image-based diagnostic system may include: a parameter collector 1 configured to at least collect environmental parameter information; a model establishment circuitry 2 configured to establish an estimation model by using image training data; and an analysis circuitry 3 configured to analyze second image information by using the estimation model and generate an analysis result corresponding to the second image information. The image training data may include first image information, and the first image information and the second image information may include information of a tongue image or information of other body parts of a user.

In some embodiments of the present disclosure, when the model establishment circuitry 2 establishes the estimation model, the image training data may be adversely affected by environmental factors or any other factor. Thus, the parameter collector 1 may be configured to collect environmental parameter information corresponding to the image training data in real time. The environmental parameter information may include at least one of brightness information or temperature information of the environment. The parameter collector 1 may also receive environmental parameter information inputted by the user, i.e., the user may input the environmental parameter information corresponding to the image training data so as to utilize the environmental parameter information when establishing the estimation model. In other words, during establishing the estimation model, the model establishment circuitry may perform the training process by combining the collected environmental parameter information with the image training data, so as to improve the accuracy when image identification and image analysis operations are performed by using the estimation model.

In addition, during establishing the estimation model, the model establishment circuitry 2 may perform the training process by using the received image training data and the environmental parameter information corresponding to the image training data. The image training data includes first image information such as a tongue image for training, and health condition data corresponding to the first image information. The health condition data includes information about a user corresponding to the first image information suffers from a cancer (e.g., esophagus cancer) or information about a probability that the user suffers from the cancer (e.g., esophagus cancer).

In some embodiments of the present disclosure, the model establishment circuitry 2 may include at least one of a wireless communication circuit and a wired communication circuit. The model establishment circuitry 2 may acquire the image training data through the wireless communication circuit or the wired communication circuit, or may directly acquire the image training data through an image collector. The parameter collector 1 may further acquire the environmental parameter information corresponding to the image training data, and transmit the environmental parameter information to the model establishment circuitry 2. The model establishment circuitry 2 may perform the training process for establishing the estimation model, by using the image training data and the environmental parameter information, so as to establish the estimation model with a high predication accuracy. In some embodiments of the present disclosure, the estimation model is established by using a neural network algorithm to perform the training process on the image training data. For example, the training process may be performed using a neural network algorithm such as a Convolutional Neural Network (CNN) algorithm or a Recurrent Neural Network (RNN) algorithm. Through the neural network algorithm, the model establishment circuitry 2 may extract feature points in the first image information, and automatically identify features of tongue images of different tongues after the training process is completed, so as to achieve health management for the user. In some embodiments of the present disclosure, the image training data may include first image information (e.g., tongue images for training) and health condition data corresponding to the first image information (e.g., identification information about a health condition of the user corresponding to the first image information), and the image training data may be used when performing the training process.

In some embodiments of the present disclosure, when the image collector acquires the first image information, the image collector may further acquire an image of the oral cavity from the first image information, and transmit the image of the oral cavity to the model establishment circuitry 2. The model establishment circuitry 2 may further perform analysis of the image of the oral cavity and combine the training process with the analysis of the image of the oral cavity, so as to further improve the accuracy of training the estimation model.

In some embodiments of the present disclosure, the model establishment circuitry 2 may perform the training process using the image training data and the environmental parameter information corresponding to the image training data as training sample data, so as to significantly improve the accuracy of training the estimation model and thereby to improve the prediction accuracy and analysis accuracy of the health condition of the user and provide more accurate analysis results of the health condition of the user.

Figure 2:
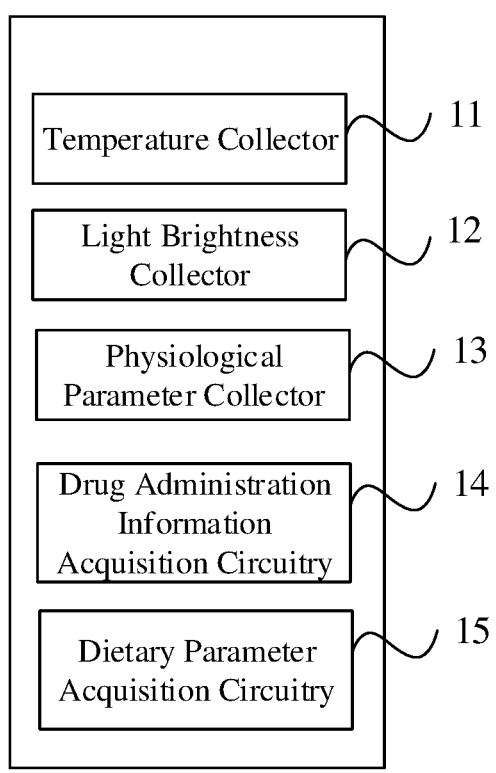
FIG. 2 is a structural schematic view of a parameter collector according to some embodiments of the present disclosure.

In some embodiments of the present disclosure, as shown in FIG. 2, the parameter collector 1 may include at least one of a temperature collector 11 configured to collect temperature information and a brightness collector 12 configured to collect brightness information of light. The temperature collector 11 may include a temperature sensor, and the brightness collector may include a brightness sensor. Optionally, the parameter collector 1 may receive the parameter information, e.g., the temperature information and the brightness information, inputted by the user via an input device. In some embodiments of the present disclosure, the first image information may correspond to one or more pieces of the collected parameter information, e.g., correspond to at least one of the temperature information and the brightness information. The first image information may be associated with the parameter information in accordance with an operation instruction inputted by the user, or the first image information may also be associated with the parameter information acquired in real time when acquiring the first image information.

The model establishment circuitry 2 may use the first image information and the parameter information (at least one of the brightness information or the temperature information) associated with the first image information as training sample data, and establish the estimation model through the neural network algorithm.

In some other embodiments of the present disclosure, the parameter collector 1 may further include a physiological parameter collector 13 configured to acquire the physiological parameter information of a user. The physiological parameter information includes one or more of body temperature information, respiratory rate information and heart rate information. In other words, considering influence on collecting an image due to strenuous exercises, the above physiological parameter collector 13 may be provided in some embodiments of the present disclosure and may include at least one of a heart rate detector, a body temperature detector and a respiratory rate detector. The heart rate detector is configured to detect the heart rate information, the body temperature detector is configured to detect the body temperature information, and the respiratory rate detector is configured to detect the respiratory rate information.

Figure 3:
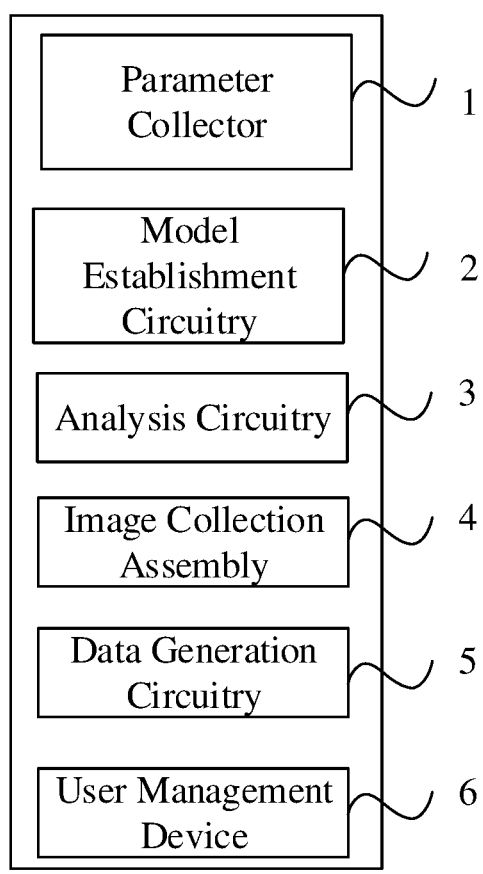
FIG. 3 is another structural schematic view of the tongue-image-based diagnostic system according to some embodiments of the present disclosure.

In order to facilitate the detection of the above physiological parameter information, the respiratory rate detector may be arranged on an image collection assembly 4 for collecting the first image information, as shown in FIG. 3. For example, in a case that a tongue image is being acquired, a respiratory rate of the user may be detected simultaneously. The body temperature detector and the heart rate detector may be arranged at positions facilitating the detection of the body temperature information and the heart rate information, respectively. For example, the body temperature detector may be arranged at a side of the image collection assembly 4 facing the user, and the heart rate detector may be directly worn on a wrist or elbow of the user. In some embodiments of the present disclosure, the physiological parameter collector 13 may also be separated from the model establishment circuitry 2, as long as the physiological parameter collector 13 may transmit the physiological parameter information to the model establishment circuitry 2.

Further, the model establishment circuitry 2 may perform the training process using the image training data, the environmental parameter information and the physiological parameter information corresponding to the image training data, or perform the training process using the image training data and the physiological parameter information, and then establish the estimation model through the neural network algorithm determined in advance. In some embodiments of the present disclosure, the more the parameter information selected as the training sample data is, the higher the accuracy of the established estimation model is.

In some embodiments of the present disclosure, the parameter collector 1 may further include a drug administration information acquisition circuitry 14 configured to acquire drug administration information about the user. The drug administration information may include a name and a dosage of a drug administrated by the user within a predetermined time period (e.g., within one week, one month or other time period). During the training process of the first image information or image correction performed on the first image information, influence of the drug administration information on the tongue image may be analyzed. In some embodiments, the parameter collector 1 may further include a dietary parameter acquisition circuitry 15 configured to acquire dietary information about the user, e.g., the dietary information about the user within a predetermined time period (e.g., within one week, one month or other time period). During the training process using the first image information or the image correction performed on the first image, influence of the dietary parameter information on the tongue image may be analyzed.

The model establishment circuitry 2 is further configured to perform the training process by using the image training data, the environmental parameter information corresponding to the image training data, at least one of (i) the physiological parameter information, (ii) the drug administration information about the user, or (iii) the dietary information, so as to establish the estimation model. In some embodiments of the present disclosure, the more the parameter information selected as the training sample data is, the higher the accuracy of the established estimation model is.

In some embodiments of the present disclosure, the model establishment circuitry 2 is further configured to validate the established estimation model. To be specific, the model establishment circuitry 2 may validate the estimation model using a plurality of groups of inputted validation data, and each group of validation data includes image information and a health estimation result corresponding to the image information. The plurality of groups of validation data may be inputted to the established estimation model so as to acquire analysis results, and then the analysis results may be compared with the health estimation results, and a coherence of the analysis results of the plurality of groups of validation data with the health estimation results is obtained. When the coherence is greater than a predetermined probability, the model establishment circuitry 2 may determine that the estimation model is validated successfully. Otherwise, the model establishment circuitry 2 may add the plurality of groups of validation data into the training sample data or acquire other sample data to continue the training process until the estimation model is validated successfully.

After the estimation model has been validated successfully, the analysis circuitry 3 may analyze the second image information based on the validated estimation model and generate an analysis result corresponding to the second image information. The second image information may include a tongue image of a user to be diagnosed.

According to some embodiments of the present disclosure, the tongue-image-based diagnostic system may establish the estimation model. Since the environmental factors, the physiological parameters, the drug administration information, the dietary information and the image training data are taken together as the training sample data, the system may significantly improve prediction accuracy of the estimation model.

FIG. 3 is another structural schematic diagram of the tongue-image-based diagnostic system according to some embodiments of the present disclosure, As compared with the diagnostic system shown in FIG. 2, the diagnostic system in FIG. 3 may include an image collection assembly 4 for acquiring image information, a data generation circuitry 5 for generating the image training data, and a user management device 6 for managing data of a user.

Figure 4:
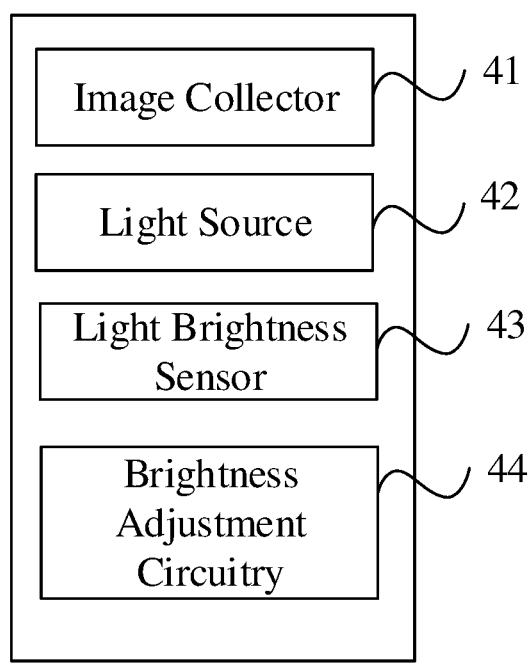
FIG. 4 is a structural schematic view of an image collection assembly according to some embodiments of the present disclosure.

As shown in FIG. 4, the image collection assembly 4 may include an image collector 41 configured to acquire image information. The image collector 41 may include at least one of a camera and a communication circuitry. The camera is configured to collect an image of a body part of the user in real time, e.g., a tongue image. The communication circuitry is configured to acquire the image information from another device or the image information uploaded by the user. The image information may be an image used for detecting the health condition of the user. After the image information is acquired, the image collector may transmit the image information to the model establishment circuitry 2 or the analysis circuitry 3, so that the model establishment circuitry 2 may use the image information to generate the estimation model or the analysis circuitry 3 may use the image information to analyze and determine the health condition of the user.

In addition, during establishing the estimation model, the image collection assembly 4 may also transmit the acquired image information to the data generation circuitry 5, so as to generate the image training data. The data generation circuitry 5 may further transmit the generated image training data to the model establishment circuitry 2 so as to establish the estimation model.

In some embodiments of the present disclosure, in order to differentiate an image for detecting the health condition from an image for establishing the estimation model, the image for establishing the estimation model and being used as the training data is called as the first image or first image information, and the image being uploaded by the user or acquired in real time and being used for detecting the health condition of the user is called as the second image or second information. These images may be obtained through the image collection assembly 4.

The data generation circuitry 5 may acquire the first image information from the image collection assembly 4, and directly transmit the first image information to the model establishment circuitry 2 for a training purpose. The data generation circuitry 5 may process the first image information, so as to increase the training sample data. To be specific, the data generation circuitry 5 may perform an image conversion operation on the first image information, and generate the image training data based on at least one of the first image information and the converted first image information. In other words, through the image conversion operation, an amount of the training sample data may be increased, thereby to improve the accuracy of the estimation model established by the model establishment circuitry 2. In some embodiments of the present disclosure, the image conversion operation may include at least one of an image translation operation or an image rotation operation.

In some embodiments of the present disclosure, the image conversion operation may further include at least one of an image segmentation operation or an image annotation operation. Optionally, the data generation circuitry 5 may performs at least one of the image translation operation, the image rotation operation, the image segmentation operation, and the image annotation operation on the first image information, so as to generate the first image information to be used as the image training data. The image segmentation operation includes segmenting the acquired image in accordance with body parts in the acquired image, and the image annotation operation includes assigning identification information corresponding to portions of the segmented image. Data labels (such as descriptive information of relevant portions) for different portions of the segmented image may also be acquired, and these data labels, the image, and the identification information may together form the image training data.

The acquired image may be an image of a tongue. During segmenting the acquired image, the acquired image may be segmented into image portions of a root of the tongue, a tip of the tongue, a middle part of the tongue and two edge parts of the tongue according to different parts of the tongue. During annotating the image, the identification information may be provided to the different parts of the tongue. Information about the user (e.g., age, gender, or the like) related to the acquired image, descriptive information about the tongue of the user, information about the user suffers from a disease (such as a cancer) or the like may also be acquired. The data generation circuitry 5 may generate the image training data based on the above information.

FIG. 4 is a structural schematic diagram of the image collection assembly according to some embodiments of the present disclosure. As shown in FIG. 4, besides the image collector 41, the image collection assembly 4 may further include a light source 42, a light brightness sensor 43 and a brightness adjustment circuitry 44.

The light source 42 may include a light-emitting diode (LED) configured to provide light having a suitable brightness value when the image is acquired by the image collector 41. The light brightness sensor 43 may collect the brightness value. The brightness adjustment circuitry 44 may adjust the brightness value of the light from the light source 42 when the brightness value collected by the light brightness sensor 43 is different from a predetermined brightness value until the brightness value collected by the light brightness sensor 43 is the same as the predetermined brightness value. When the brightness value collected by the light brightness sensor 43 is the same as the predetermined brightness value, the brightness adjustment circuitry 42 may control the image collector 41 to collect the image information. In other words, the brightness adjustment circuitry 44 may receive the brightness value from the light brightness sensor 43, compare the brightness value with the predetermined brightness value, and transmit a signal to the light source 42 so as to cause the light source 42 to adjust the brightness value of the light until the brightness value collected by the light brightness sensor 43 is the same as the predetermined brightness value.

In some embodiments of the present disclosure, although the light brightness sensor 43 is arranged in the image collection assembly 4 in FIG. 4, the light brightness sensor 43 may also be a light brightness collector for collecting the brightness value in the parameter collector 1, or be a separate light brightness sensor. The brightness value of the light generated by the light source 41 may be adjusted in accordance with the brightness value collected by the light brightness sensor, and it may be ensured that brightness values are consistent when the image collector 41 acquires images.

In some embodiments of the present disclosure, the image collector 41 may also be formed as a terminal, e.g., a mobile phone, camera, or the like. The image collector 41 may directly acquire image information of a body part of the user to be detected, e.g., an image of the tongue; or the image collector 41 may also receive image information uploaded by the user. Upon acquisition of the image information, the image collector 41 may directly transmit the image information to the analysis circuitry 3. The analysis circuitry 3 may analyze the image information, and transmit an analysis result back to the terminal. The user may view the analysis result on the terminal and acquire the health condition of the user.

In some embodiments of the present disclosure, the image collector 41 may also transmit the image information to the user management device 6 via a network. The user management device 6 may create a link (such as a data link) between the image collector 41 and the analysis circuitry 3. The creation of the data link between the image collector 41 and the analysis circuitry 3 by the user management device 6 may specifically include the following: the user management device 6 stores the image information sent from the image collector 41 in association with the information about the user, transmits the image information to the analysis circuitry 3 for analyzing the health condition, receives the analysis result from the analysis circuitry 3, stores the analysis result in association with the information about the user, and transmits the analysis result to the user, so that the user may achieve inquiry and management of his or her health condition. In other words, the user management device 6 may store the image information uploaded by the user, the information about the user and the analysis result sent back from the analysis circuitry. When the user needs to view information relevant to the user, the user may send a request to the user management device 6 to inquire the information. The user management device may be formed as an application APP in a mobile terminal, or a separate server. The server may be structured by electronic circuits, software or a combination of the electronic circuits and the software. The server may also be formed as any one of a computer chip, a processor, a storage, or any combination thereof. The analysis circuitry 3 and the model establishment circuitry 2 may also be formed in a separate server. Hence, any electronic circuit or any computer software capable of implementing the user management device 6, the analysis circuitry 3 and the model establishment circuitry 2 of the present disclosure falls within the scope of the present disclosure.

The tongue-image-based diagnostic system in some embodiments of the present disclosure may prevent and detect a disease, and since the environmental parameters, the physiological parameter and other parameters are taken as a part of the training sample data during establishing the estimation model, the accuracy of the estimation model may be increased significantly, thereby facilitating the analysis and prevention of a disease.

Figure 5:
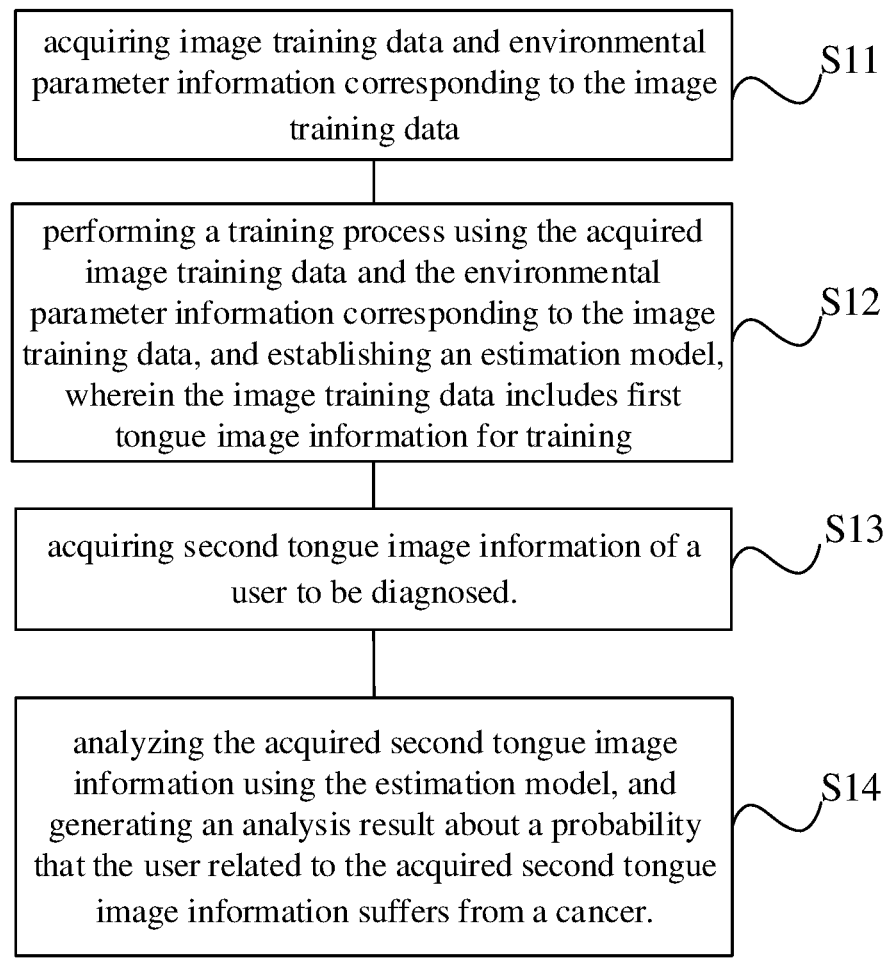
FIG. 5 is a flowchart of a tongue-image-based diagnostic method according to some embodiments of the present disclosure.

The present disclosure further provides in some embodiments a tongue-image-based diagnostic method. The diagnostic method may be performed by the above-mentioned tongue-image-based diagnostic system. Specifically, as shown in FIG. 5, the diagnostic method may include the following steps S11-S14.

Step S11: acquiring image training data and environmental parameter information corresponding to the image training data.

Step S12: performing a training process using the acquired image training data and the environmental parameter information corresponding to the image training data, and establishing an estimation model, wherein the image training data includes first tongue image information for training.

Step S13: acquiring second tongue image information of a user to be diagnosed.

Step S14: analyzing the acquired second tongue image information based on the estimation model, and generating an analysis result about a probability that the user related to the acquired second tongue image information suffers from a cancer.

In some embodiments of the present disclosure, the environmental parameter information includes at least one of temperature information and brightness information.

In some embodiments of the present disclosure, before Step S11, the diagnostic method may further include: acquiring at least one of physiological parameter information, drug administration information or dietary parameter information; and the performing a training process using the acquired image training data and the environmental parameter information corresponding to the image training data in the Step S11 may include performing the training process using the image training data, the environmental parameter information corresponding to the image training data, and at least one of (i) the physiological parameter information, (ii) the drug administration information, or (iii) the dietary information.

In some embodiments of the present disclosure, before Step S11, the diagnostic method further includes: acquiring the first tongue image information; performing an image conversion operation on the first tongue image information; and generating the image training data based on at least one of the first tongue image information or the converted first tongue image information.

The image conversion operation in the above embodiments of the present disclosure may include at least one of an image translation operation, an image rotation operation, an image segmentation operation or an image annotation operation.

In some embodiments of the present disclosure, the diagnostic method further includes: validating the estimation model; after the validation of the estimation module is successful, analyzing the second tongue image information using the validated estimation model; and generating the analysis result corresponding to the second tongue image information.

In some embodiments of the present disclosure, the image training data includes tongue images for training and health condition data corresponding to the tongue images, and the health condition data includes information about a user suffers from a cancer or information about a probability that a user suffers from a cancer.

It is appreciated that, the functions and/or steps performed by the diagnostic system mentioned above in the present disclosure may also be applied to the diagnostic method provided by the present disclosure.

The diagnostic method in some embodiments of the present disclosure may prevent and detect a disease. Since the environmental parameters, the physiological parameter or other parameters are taken as a part of the training sample data during establishing the estimation model, the analysis accuracy of the estimation model may be significantly improved, thereby facilitating the analysis and prevention of a disease.

The present disclosure further provides in some embodiments a tongue-image-based diagnostic device. The tongue-image-based diagnostic device includes a storage and a processor. The storage is configured to store therein a computer program executable by the processor. The processor is configured to execute the compute program to implement the above-mentioned tongue-image-based diagnostic method, and a same technical effect may also be attained.

The present disclosure further provides in some embodiments a computer readable storage medium which stores therein a computer program executable by a computer processor. When the computer processor executes the computer program, the computer processor may implement the above-mentioned diagnostic method, and a same technical effect may be attained. The computer readable storage medium may be a volatile or nonvolatile storage medium, or a transient or non-transient storage medium, e.g., Read Only Memory (ROM), Random Access Memory (RAM), magnetic discs or optical discs.

It may be understood by one skilled in the art that implementation of an electronic device to which the above diagnostic method is applied may be similar to the implementation of the above diagnostic device, and thus will not be particularly defined herein.

It should be noted that, division for the above circuitry is merely based on logic functions of the above circuitry, and in actual application, the circuitry or the assemblies may be completely or partially integrated into one physical entity, or physically separated from each other. The circuitry may completely be implemented by software and processing elements invoking the software, or completely be implemented by hardware, partly be implemented by software and processing elements invoking the software and partly be implemented by hardware. For example, the model establishment circuitry 2, the parameter collector 1 and the analysis circuitry 3 may be processing elements arranged separately, or be integrated into a chip of the above-mentioned device. In addition, the circuitry may also be stored in the storage of the above-mentioned device in a form of programs, and be called and executed by a processing element of the above-mentioned device so as to achieve the functions of the circuitry. The other circuitry may be implemented in a similar manner. All or parts of the circuitry may be integrated together or arranged separately. Here, the circuitry, units, assemblies, or device may be an Integrated Circuit (IC) having a signal processing capability.

For example, the above circuitry or device may be one or more ICs capable of implementing the above-mentioned method, e.g., one or more Application Specific Integrated Circuits (ASICs), one or more Digital Signal Processors (DSPs), or one or more Field Programmable Gate Array (FPGA). When the above method is implemented by the software and the processing element invoking the software, the processing element may be a general-purpose processor, e.g., a Central Processing Unit (CPU) or any other processor capable of invoking the software. The circuitry may be implemented in a form of system-on-chip (SOC).

The above embodiments are only illustrative embodiments of the present disclosure, but the present disclosure is not limited thereto. The scope of the present disclosure is defined in the appended claims. One skilled in the art may make further modifications, equivalent substitution, or improvements without departing from the spirit and scope of the present disclosure, and these modifications, equivalent substitution, or improvements also fall within the scope of the present disclosure.

What is claimed is:

1. A tongue-image-based diagnostic system, comprising:
a parameter collector configured to acquire parameter information corresponding to image training data in real time, wherein the parameter collector comprises: a temperature collector configured to collect temperature information, a brightness collector configured to collect brightness information, and a physiological parameter collector configured to collect physiological parameter information, wherein the parameter collector is further configured to acquire at least one of drug administration information or dietary parameter information of a user;
a model establishment circuitry configured to perform a training process using a neural network algorithm and using the image training data and the parameter information to establish an estimation model, wherein the image training data comprises a first tongue image for training, each first tongue image is associated with the temperature information and the brightness information, the physiological parameter information and at least one of the drug administration information or the dietary parameter information of the user which are acquired in real time when acquiring the first tongue image; and
an analysis circuitry configured to analyze acquired image information using the estimation model, and to generate at least an analysis result about a probability that the user related to the acquired image information suffers from a cancer, wherein the acquired image information comprises a second tongue image of the user to be diagnosed.

2. The diagnostic system according to claim 1, wherein the physiological parameter information comprises at least one of body temperature information, respiratory rate information or heart rate information of a user, and
the model establishment circuitry is further configured to perform the training process using the image training data, the parameter information corresponding to the image training data and the physiological parameter information, and establish the estimation model.

3. The diagnostic system according to claim 1, wherein the model establishment circuitry is further configured to validate the estimation model, and
the analysis circuitry is further configured to, if the model establishment circuitry successfully validates the estimation model, analyze the second tongue image using the validated estimation model and generate the analysis result corresponding to the second tongue image.

4. The diagnostic system according to claim 1, further comprising:
an image collection assembly comprising an image collector and configured to acquire at least one of the first tongue image and the second tongue image with the image collector, and transmit the first tongue image to the model establishment circuitry and transmit the second tongue image to the analysis circuitry.

5. The diagnostic system according to claim 4, wherein the image collection assembly further comprises:
a light source configured to generate light;
a light brightness sensor configured to collect a brightness value of the environment; and
a brightness adjustment circuitry configured to:
receive the brightness value from the light brightness sensor,
compare the received brightness value with a predetermined brightness value,
if the received brightness value is different from the predetermined brightness value, adjust the brightness value of the light generated by the light source until the brightness value collected by the light brightness sensor is the same as the predetermined brightness value, and
if the brightness value collected by the light brightness sensor is the same as the predetermined brightness value, control the image collector to collect image information.

6. The diagnostic system according to claim 1, wherein the image training data further comprises health condition data corresponding to the first tongue image, and the health condition data comprises information about the user suffering from the cancer or information about a probability that the user suffers from the cancer.

7. The diagnostic system according to claim 4, wherein the image collector is further configured to acquire an oral image of the user when acquiring the first tongue image, and the model establishment circuitry is further configured to analyze the oral image.

8. The diagnostic system according to claim 3, wherein the model establishment circuitry is further configured to:
validate the estimation model using a plurality of groups of validation data, wherein each group of validation data comprises image information and a health estimation result corresponding to the image information; and
based on coherence of validation results of the plurality of groups of validation data with the health estimation result being greater than a predetermined probability, determine that the estimation model is validated successfully.

9. A tongue-image-based diagnostic method, comprising:

acquiring parameter information corresponding to image training data in real time, wherein the parameter information comprises temperature information, brightness information, physiological parameter information and at least one of drug administration information or dietary parameter information of a user;

performing a training process using a neural network algorithm and using the image training data and the parameter information, and establishing an estimation model, wherein the image training data comprises a first tongue image for training, each first tongue image is associated with the temperature information and the brightness information, the physiological parameter information and at least one of the drug administration information or the dietary parameter information of the user which are acquired in real time when acquiring the first tongue image; and analyzing acquired image information using the estimation model, and generating an analysis result about a probability that the user corresponding to the acquired image information suffers from a cancer, wherein the acquired image information comprises a second tongue image of the user to be diagnosed.

10. The diagnostic method according to claim 9, further comprising:

validating the estimation model;

if the estimation model is validated successfully, analyzing the second tongue image using the validated estimation model; and generating the analysis result corresponding to the second tongue image.

11. The diagnostic method according to claim 10, wherein the image training data further comprises health condition data of the user corresponding to the first tongue image, and the health condition data comprises information about the user corresponding to the first tongue image suffering from a cancer or information about a probability that the user suffers from the cancer.

12. A tongue-image-based diagnostic system, comprising:
a processor, and
a memory storing computer programs executable by the processor,
wherein the computer programs, when executed by the processor, cause the processor to perform the diagnostic method according to claim 9.

13. A tongue-image-based diagnostic system, comprising:
a parameter collector configured to acquire parameter information corresponding to image training data in real time, wherein the parameter collector comprises: a temperature collector configured to collect temperature information, a brightness collector configured to collect brightness information, and a physiological parameter collector configured to collect physiological parameter information, wherein the parameter collector is further configured to acquire at least one of drug administration information or dietary parameter information of a user;
a model establishment circuitry configured to perform a training process using a neural network algorithm and using the image training data and the parameter information to establish an estimation model, wherein the image training data comprises first tongue image for training, and each first tongue image is associated with the temperature information the brightness information, the physiological parameter information and at least one of the drug administration information or the dietary parameter information of the user which are acquired in real time when acquiring the first tongue image;

an image collection assembly configured to acquire second tongue image;

a user management circuitry configured to store the second tongue image with information about the user, and transmit the second tongue image to an analysis circuitry; and the analysis circuitry configured to analyze the second tongue image using the estimation model, and to generate at least an analysis result about a probability that the user related to the acquired image information suffers from a cancer, wherein the second tongue image comprises tongue image of the user to be diagnosed;

wherein the user management circuitry is further configured to receive the analysis result from the analysis circuitry and store the analysis result with the information about the user, to establish a personal profile database for each user.

14. The diagnostic method according to claim 9, wherein:
after performing the training process using image training data and the parameter information, and establishing the estimation model, the diagnostic method further comprises:

acquiring the second tongue image; and storing the second tongue image with the information about the user; and after the analyzing acquired image information using the estimation model, and generating an analysis result about a probability that a user corresponding to the acquired image information suffers from a cancer, the diagnostic method further comprises:

storing the analysis result with the information about the user, to establish a personal profile database for each user.

15. The diagnostic system according to claim 1, further comprising:

a data generation circuitry configured to perform an image conversion operation on the first tongue image information, and generate the image training data based one at least one of the first tongue image information or the converted first tongue image information.

16. The diagnostic system according to claim 15, wherein the image conversion operation comprises at least one of an image translation operation or an image rotation operation, or at least one of an image segmentation operation or an image annotation operation.

17. The diagnostic method according to claim 9, wherein before performing a training process using received image training data and the parameter information, and establishing an estimation model, the diagnostic method further comprises:

acquiring the first tongue image information;

performing an image conversion operation on the acquired first tongue image information; and generating the image training data using at least one of the first tongue image information or the converted first tongue image information.

18. The diagnostic method according to claim 17, wherein the performing an image conversion operation on the acquired first tongue image information comprises:

performing at least one of an image segmentation operation or an image annotation operation on the first tongue image information, or performing at least one of an image translation operation or an image rotation operation on the first tongue image information.

\* \* \* \* \*